(12) United States Patent
Liu

(10) Patent No.: US 10,611,788 B2
(45) Date of Patent: *Apr. 7, 2020

(54) CATALYTIC GLYCOSYLATION WITH DESIGNER THIOGLYCOSIDE AND NOVEL PROTECTING GROUPS FOR SAME AND FOR SYNTHESIS OF OLIGOSACCHARIDES

(71) Applicant: UNIVERSITY OF PITTSBURGH—OF THE COMMONWEALTH SYSTEM OF HIGHER EDUCATION, Pittsburgh, PA (US)

(72) Inventor: Xinyu Liu, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/192,680

(22) Filed: Jun. 24, 2016

(65) Prior Publication Data

US 2017/0022237 A1 Jan. 26, 2017
US 2019/0270763 A9 Sep. 5, 2019

Related U.S. Application Data

(62) Division of application No. 13/912,048, filed on Jun. 6, 2013, now Pat. No. 9,399,655.

(60) Provisional application No. 61/656,366, filed on Jun. 6, 2012, provisional application No. 61/677,993, filed on Jul. 31, 2012.

(51) Int. Cl.
| | | |
|---|---|---|
| *C07H 1/00* | (2006.01) |
| *C07C 69/88* | (2006.01) |
| *C07C 69/94* | (2006.01) |
| *C07C 65/24* | (2006.01) |
| *C07C 59/66* | (2006.01) |
| *C07H 15/203* | (2006.01) |

(52) U.S. Cl.
CPC ............. *C07H 1/00* (2013.01); *C07C 59/66* (2013.01); *C07C 65/24* (2013.01); *C07C 69/88* (2013.01); *C07C 69/94* (2013.01); *C07H 15/203* (2013.01); *Y02P 20/55* (2015.11)

(58) Field of Classification Search
None
See application file for complete search history.

(56) References Cited

U.S. PATENT DOCUMENTS 5,278,303 A * 1/1994 Krepinsky ............. C07H 15/04
527/300

OTHER PUBLICATIONS

Codee, C. R. Chimie 14 (2011) 178-193.*
Adhikari, ACS Catal. 2013, 3, 57-60, published online Nov. 28, 2012.*
Yang, Tetrahedron Letters 53 (2012) 5231-5234, available online Jul. 20, 2012.*

* cited by examiner

*Primary Examiner* — Layla D Berry
(74) *Attorney, Agent, or Firm* — Paul D. Bangor, Jr., Esquire; Clark Hill, PLC

(57) ABSTRACT

A catalytic glycosylation method comprising: installing thioether to an anomeric carbon of a carbohydrate; and catalytically activating the thioether with a non-oxophilic Lewis acid. The thioether may comprise an anomerically stable thioether leaving group. The catalytic glycosylation method may further comprise: utilizing an acid-sensitive ester protecting group as permanent protecting group or using a reactivity-based one-pot glycosylation that employs a single-component catalyst to accelerate an oligosaccharide assembly process. A protecting group to mask hydroxyl functionalities in the production of oligosaccharides, natural products or any molecule having a hydroxyl group comprising an acid-labile ester protecting group.

3 Claims, 6 Drawing Sheets

FIG 6
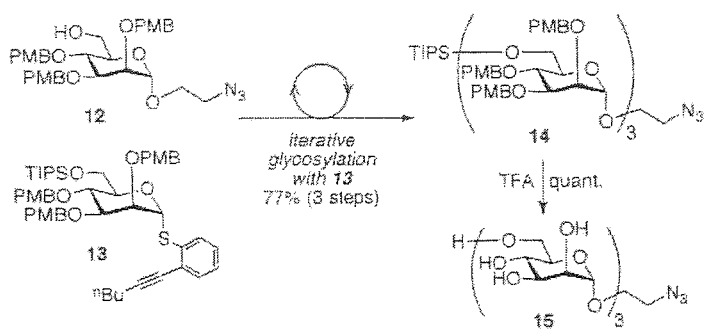
FIG 7
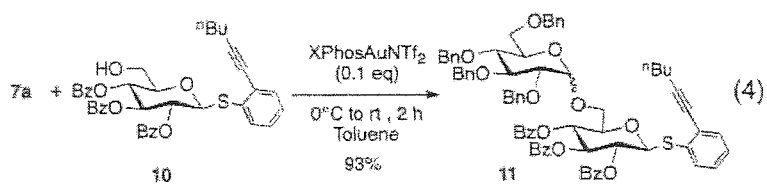
FIG 8
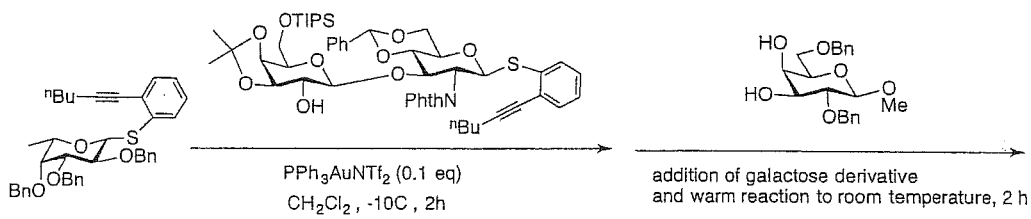
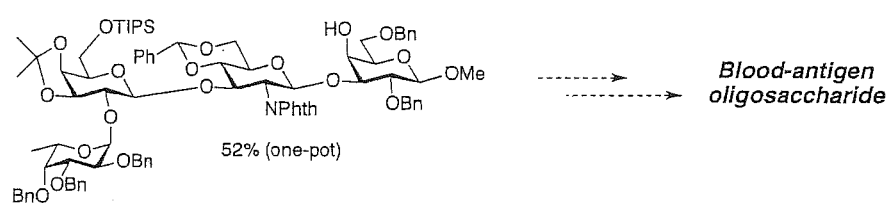

FIG 9

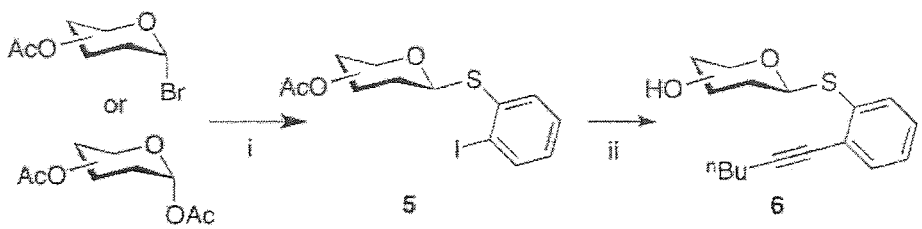

| Entry | Substrate | 5 (yield) | 6 (yield) |
|---|---|---|---|
| 1 | acetobromo-α-D-glucose | 5a (86%) | 6a (97%) |
| 2 | acetobromo-α-D-galactose | 5b (83%) | 6b (99%) |
| 3 | D-mannose pentaacetate | 5c (90%) | 6c (90%) |
| 4 | N-phthaloyl-β-D-glucosamine tetraacetate | ds (90%) | 6d (99%) |

FIG 10

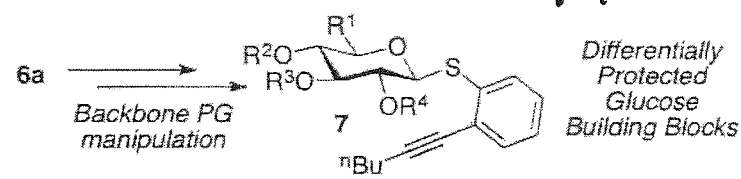

Differentially Protected Glucose Building Blocks

| Entry | Key Transformation | Product (yield) |
|---|---|---|
| 1 | O-Alkylation | 7a (95%)[a] ($R^1$=CH$_2$OBn, $R^2$=$R^3$=$R^4$=Bn) |
| 2 | O-Acylation | 1 (96%)[a] ($R^1$=CH$_2$OBz, $R^2$=$R^3$=$R^4$=Bz) |
| 3 | Reductive benzylidene opening | 7b (92%)[b] ($R^1$=CH$_2$OBn, $R^2$=H, $R^3$=$R^4$=Bn) |
| 4 | Acetal hydrolysis (acid) | 7c (87%)[b] ($R^1$=CH$_2$OBn, $R^2$=H, $R^3$=$R^4$=Bn) |
| 5 | oxidation of 1° alcohol to carboxylic acid | 7d (87%)[c] ($R^1$=COOH, $R^2$=$R^3$=$R^4$=Bz) |

Figure 11    *Base-catalyzed* cleavage of ester
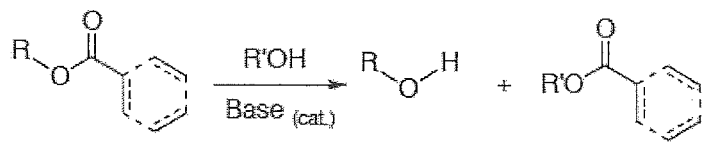
*Acid-catalyzed assisted* cleavage of ester
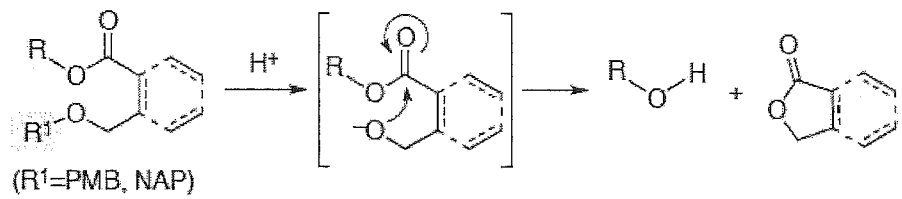
(R¹=PMB, NAP)
Figure 12
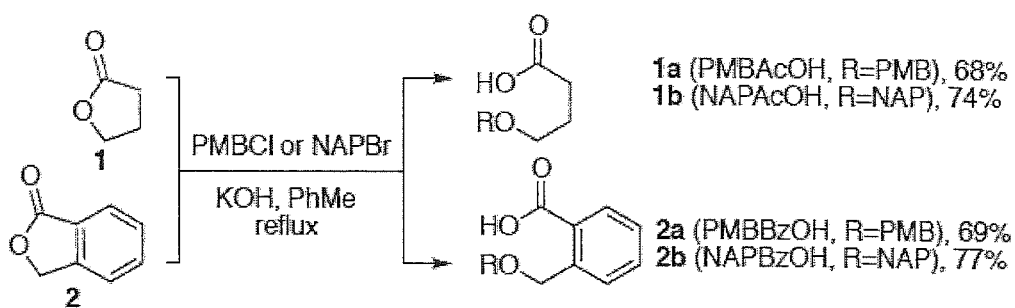
Figure 13
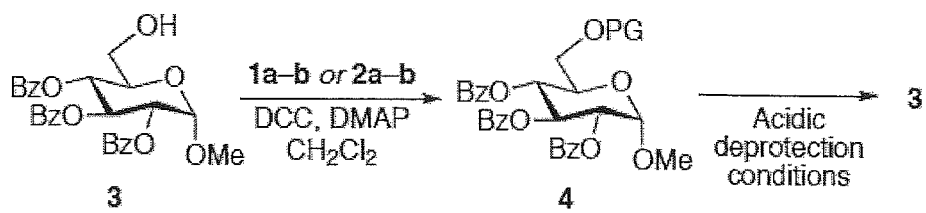
| Entry | 3→4 yield | 4→3 conditions, yield |
|---|---|---|
| 1 | 4a (PG=PMBAc), 93% | TFA/PhMe (1:10, v/v), rt, 1 h, 98% |
| 2 | 4b (PG=PMBBz), 97% | TFA/PhMe (1:10, v/v), rt, 5 min, 98% |
| 3 | 4c (PG=NAPAc), 95% | a) TFA/PhMe (1:10, v/v), rt, 1 h, N.R. b) TFA/PhMe (10:1, v/v), rt, 8 h, 94% |
| 4 | 4d (PG=NAPBz), 97% | TFA/PhMe (10:1, v/v), rt, 1.5 h, 96% |

CATALYTIC GLYCOSYLATION WITH DESIGNER THIOGLYCOSIDE AND NOVEL PROTECTING GROUPS FOR SAME AND FOR SYNTHESIS OF OLIGOSACCHARIDES

RELATED APPLICATIONS

The present application is a DIVISIONAL of copending U.S. patent application Ser. No. 13/912,048 entitled "CATALYTIC GLYCOSYLATION WITH DESIGNER THIOGLYCOSIDE AND NOVEL PROTECTING GROUPS FOR SAME AND FOR SYNTHESIS OF OLIOGOSACCHARIDES" and filed Jun. 6, 2013 (the "'048 Application"), the entirety of which is incorporated herein by reference for all purposes. Each of the present application and the '048 Application claims priority benefit under 35 U.S.C. § 119(e) of U.S. Provisional Application No. 61/656,366, filed Jun. 6, 2012, and of U.S. Provisional Application No. 61/677,993, filed Jul. 31, 2012.

TECHNICAL FIELD

The present disclosure generally relates to catalytic glycosylation methods and protecting groups for the same and for synthesis of oligosaccharides, natural products or any molecule having a hydroxyl group.

BACKGROUND

Oligosaccharide is the third most abundant biopolymer in a living system, next to nucleic acid and proteins. The biological significance of oligosaccharide is undisputable, yet the rapid preparation of homogeneous oligosaccharide by automation, analogues to the synthesis of DNA/RNA oligonucleotides and peptides, remains far beyond reach.

Two of the most fundamental issues in modern chemical synthesis of oligosaccharides that requires innovation are 1) chemical glycosylation method that permits the robust construction of desired glycosidic linkage, 2) protecting groups that can be strategically applied to the blockage of designated hydroxyl, amino, carboxyl groups, yet can be readily removed to release the desired oligosaccharide. The present disclosure addresses both of these fundamental issues with respect to modern chemical synthesis of oligosaccharides.

FIG. 1 shows a comparison of known catalytic glycosylation methods with a preferred catalytic glycosylation method of the present disclosure. Currently available chemical glycosylating agents largely fall into two categories. One type is based on anomerically labile leaving groups, which can be activated by catalytic amount of a Lewis acid. The classical example is trichloroacetaimidate based glycosylating agent (Schmidt donor), but also includes glycosyl phosphite and ester-based glycosylating agent. These glycosylating agents do not tolerate acid/base treatment so that the leaving group itself has to be installed in the last step of the monosaccharide or oligosaccharide building block preparation prior to the actual glycosylation event as shown in FIG. 1. From a practical point-of-view, this is a critical drawback, as the preparation of any imidate-type glycosylating agent requires the pre-selection of a protecting group to mask the anomeric center and remove it at the penultimate step to install the leaving group.

The other type of widely used glycosylating agent is based on anomerically stable leaving group. The classical examples are thioether or n-pentenyl ether based glycosylating agents. While these types of leaving groups are anomerically stable, they have to be activated by more than stoichiometric amount of activator and require the usage of extra component, such as bulky non-nucleophilic amine base to effectively quench the in-situ generated acid.

Therefore, one would envision that an ideal type of chemical glycosylating agent should combine the catalytic activator-feature of glycosyl imidate and the anomeric stable feature of thioglycoside. Preferred glycosylation methods of the present disclosure fulfill this criterion. Moreover, the most commonly used activators in chemical glycosylation are highly oxophilic Lewis acids or thiophilic electrophiles. In both cases, the reaction will be carried out in an acidic environment, which not only calls for the extra non-nucleaphilic base (not atom-economical) but also preludes the application of acid-sensitive protecting groups as permanent protecting groups in oligosaccharide assembly. The preferred glycosylation methods of the present disclosure provide a new class of thioglycoside which permits the application of cationic gold(I) complex as an activator, which is carbophilic rather than oxophilic, thus circumventing the limitation associated with the usage of oxophilic Lewis acid with conventional glycosylation agents.

Another fundamental issue in modern chemical synthesis of oligosaccharides is that too many orthogonal protecting groups for hydroxyl and amino functionalities are introduced at the early stage of the process. While the adoption of this strategy is clearly understandable, as the carbohydrate backbone contains a myriad of hydroxyls and amines which have to be "chemically protected" properly in order to achieve regioselective chain elongation, the excess orthogonalities in terms of chemical reactivity that are present in a protected oligosaccharide make the late stage chemical synthesis tedious which often results in unpredictable failure.

Benzyl ethers and ester-type of protecting groups are two most commonly used hydroxyl protecting groups in carbohydrate synthesis that requires different chemical treatment for removal. While benzyl ethers are usually sensitive to hydrogenolysis and acid, esters are sensitive to base-catalyzed hydrolysis. Within the present disclosure, it is desirable to design a series of hydroxyl protecting groups that retain the basic properties of benzyl ethers and esters, but can be deprotected by a common type of chemical reagent, acid. This aspect of the present disclosure will dramatically speed up the chemical synthesis of oligosaccharide, particularly allowing for the automation process, when coupled with a glycosylating agent that does not require strong acid for activation.

SUMMARY

One aspect of a preferred embodiment of the present disclosure comprises a catalytic glycosylation method comprising: installing thioether to an anomeric carbon of a carbohydrate; and catalytically activating the thioether with a non-oxophilic Lewis acid.

In another aspect of a preferred catalytic glycosylation method of the present disclosure, the thioether comprises an anomerically stable thioether leaving group.

In a further aspect, a preferred catalytic glycosylation method further comprises utilizing an acid-sensitive ester protecting group as permanent protecting group.

In yet another aspect, a preferred catalytic glycosylation method further comprises using a reactivity-based one-pot glycosylation that employs a single-component catalyst to accelerate an oligosaccharide assembly process.

In a further aspect, a preferred catalytic glycosylation method further comprises utilizing an application of a 100%-PEG-based polymer as insoluble support for solid-phase oligosaccharide synthesis.

In yet an additional aspect, a preferred catalytic glycosylation method further comprises utilizing a designer thioglycoside that retains basic properties of a parental thioglycoside, including the ease of preparation and toleration of backbone protecting group manipulation.

In yet another aspect, a preferred catalytic glycosylation method further comprises applying an activator permitting an application of highly acid-sensitive protecting groups; applying a 100%-PEG-based polymer as insoluble support for solid-phase oligosaccharide synthesis to streamline an oligosaccharide assembly.

In another aspect of a preferred catalytic glycosylation method of the present disclosure the activator is carbophilic In another aspect of a preferred catalytic glycosylation method of the present disclosure the activator is a cationic gold(I) complex.

Another aspect of a preferred embodiment of the present disclosure comprises a method of synthesizing an oligosaccharide, comprising the steps of: tethering an acetyl ester and a benzoyl ester to a saccharide with an alcohol group; and protecting the alcohol group with an acid-labile ester protecting group.

In a further aspect, a preferred method of synthesizing an oligosaccharide further comprises the step of deprotecting the ester group by acid treatment.

An additional aspect of a preferred embodiment of the present disclosure comprises a method of synthesizing an oligosaccharide comprising the step of activating a thioglycoside with a non-oxophilic Lewis acid.

In another aspect of a preferred method of synthesizing an oligosaccharide of the present disclosure the Lewis acid comprises a cationic gold(I) complex.

A further aspect of a preferred embodiment of the present disclosure comprises a method of synthesizing an oligosaccharide, comprising the steps of: tethering an acetyl ester and a benzoyl ester to a thioglycoside with an alcohol group; protecting the alcohol group with an acid-labile ester protecting group; deprotecting the ester group by acid treatment; and activating the thioglycoside with a non-oxophilic Lewis acid.

In another aspect of a preferred method of synthesizing an oligosaccharide of the present disclosure the Lewis acid comprises a cationic gold(I) complex.

Another aspect of a preferred embodiment of the present disclosure comprises a protecting group to mask hydroxyl functionalities in the production of oligosaccharides, natural products or any molecule having a hydroxyl group comprising an acid-labile ester protecting group.

In another aspect of a preferred protecting group of the present disclosure, the acid-labile ester protecting group is selected from a group consisting of an acetyl ester tethered with a para methoxybenzyl (PMB) ether, an acetyl ester tethered with a napthyl methyl (NAP) ether, a benzoyl ester tethered with a PMB ether and a benzoyl ester tethered with an NAP ether.

In a further aspect of a preferred protecting group of the present disclosure, the tethering of an acetyl ester or a benzoyl ester with an alcohol group that is protected with an acid-labile ester protecting group can be de-protected by an acid.

BRIEF DESCRIPTION OF THE DRAWINGS

The present disclosure is illustrated by way of example and not limitation in the figures of the accompanying drawings, in which:

FIG. 6 shows yet another preferred catalytic glycosylation method of the present disclosure.

FIG. 7 illustrates reactivity-based glycosylation according to preferred embodiments of catalytic glycosylation methods of the present disclosure.

FIG. 8 illustrates additional reactivity-based glycosylation according to preferred embodiments of catalytic glycosylation methods of the present disclosure.

FIG. 9 shows preferred processes for attaching the designed thioethers to carbohydrates and transforming to the designed glycosylating agents with respect to preferred catalytic glycosylation methods of the present disclosure.

FIG. 10 illustrates the compatibility of preferred glycosylation agents to known protecting group manipulations for use in preferred catalytic glycosylation methods of the present disclosure.

FIG. 11 illustrates differences between known protecting groups (top) and preferred acid-labile ester protecting groups for use in preferred methods of the present disclosure.

FIG. 12 illustrates preferred examples of acid-sensitive groups according to preferred embodiments of using novel protecting groups of the present disclosure.

FIG. 13 illustrates preferred acidic conditions for removing acid-labile ester protecting groups according to preferred embodiments of the present disclosure.

DETAILED DESCRIPTION OF PREFERRED EMBODIMENTS

The following description, taken in conjunction with the referenced drawings, is presented to enable one of ordinary skill in the art to make and use the disclosure and to incorporate it in the context of particular applications. Various modifications, as well as a variety of uses in different applications, will be readily apparent to those skilled in the art, and the general principles, defined herein, may be applied to a wide range of aspects. The present disclosure is not intended to be limited to the aspects disclosed herein. Instead, it is to be afforded the widest scope consistent with the disclosed aspects.

In essence, the present disclosure details the rational design of preferred anomerically stable thioglycosides that can be catalytically activated by cationic gold (I) complex. The glycosylating methods/system according to preferred embodiments of the present disclosure are novel, as they represent the first disclosed glycosylation platform which features an anomerically stable leaving group that can be activated by a catalytic amount of a single component activator. The activator itself (cationic gold(I) complex) is a non-oxophilic Lewis acid that permits the application of highly acid-sensitive protecting groups, as described herein, as global protecting groups to dramatically streamline the complex oligosaccharide synthesis. The overall system is both robust and modular in terms of the glycosylating agent itself and the activator, the reactivity of which can be readily tuned to streamline the oligosaccharide assembly process.

Figure 1:
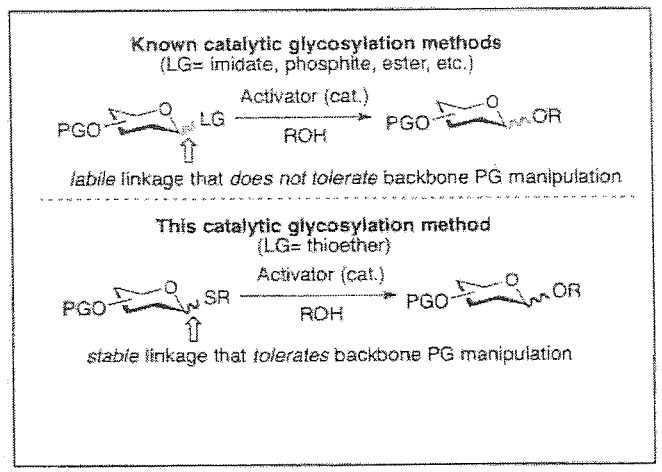
FIG. 1 shows a comparison of known catalytic glycosylation methods (top) with a preferred catalytic glycosylation method of the present disclosure (bottom).
Figure 2:
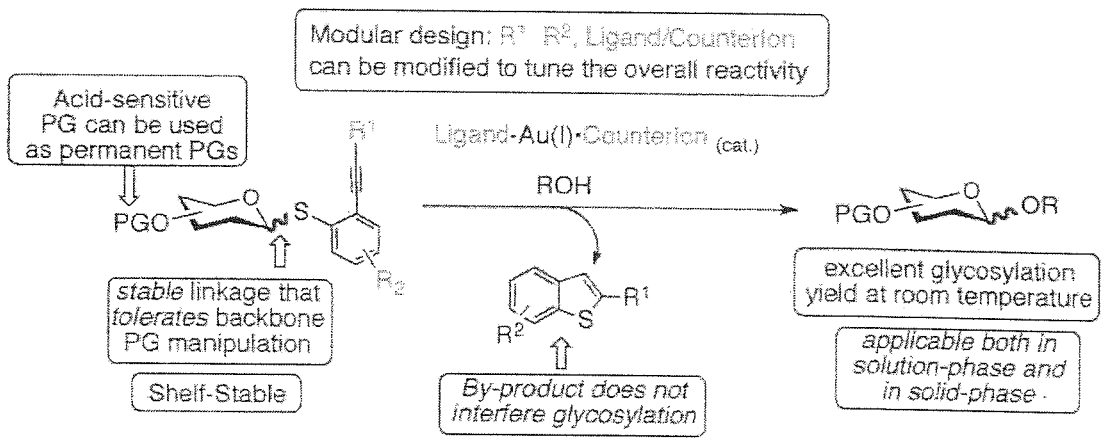
FIG. 2 shows a summary of the novel features of the glycosylating methods/systems according to preferred embodiments of the present disclosure.

FIG. 2 shows a summary of the novel features of the glycosylating method/system according to preferred embodiments of the present disclosure including:

A preferred and the first catalytic glycosylation system that features an anomerically stable thioether leaving group.

The preferred catalytic glycosylation methods/systems permit the application of highly acid-sensitive protecting groups as permanent protecting group using a series of preferred acid-sensitive ester type protecting groups described herein.

The preferred catalytic glycosylation methods/systems permit the reactivity-based one-pot glycosylation that employs a single-component catalyst that dramatically accelerates the oligosaccharide assembly process.

The preferred catalytic glycosylation methods/systems permit the application of 100%-PEG-based polymer as insoluble support for solid-phase oligosaccharide synthesis which cannot be achieved with traditional oxophilic Lewis acid activator, as they will bind the PEG backbone and diminish their activities as activators.

The designer thioglycoside according to preferred embodiments of the present disclosure retains the basic properties of parental thioglycoside, including the ease of preparation and toleration of backbone protecting group manipulation, an essential feature for preparative purpose.

Figure 3:
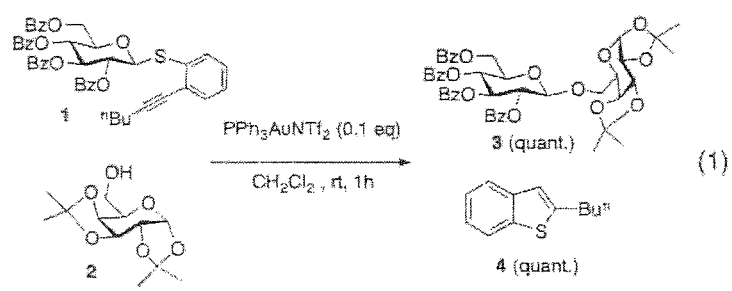
FIG. 3 illustrates a first preferred catalytic glycosylation method of the present disclosure.
Figure 4:
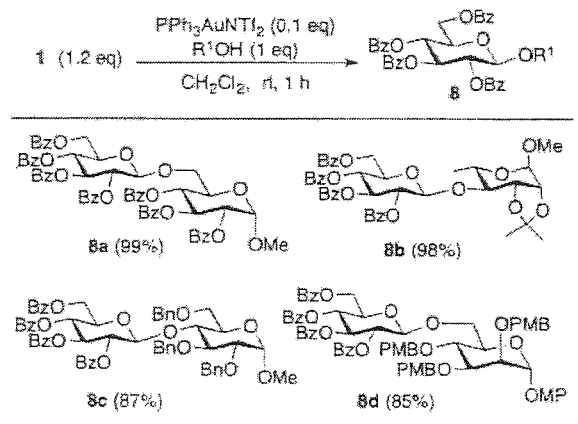
FIG. 4 shows another preferred catalytic glycosylation method of the present disclosure.
Figure 5:
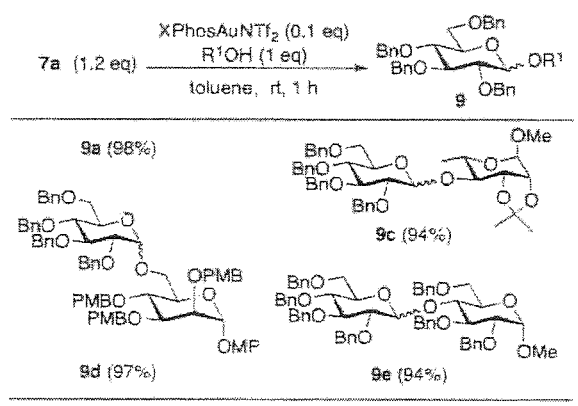
FIG. 5 illustrates an additional preferred catalytic glycosylation method of the present disclosure.
Figure 14:
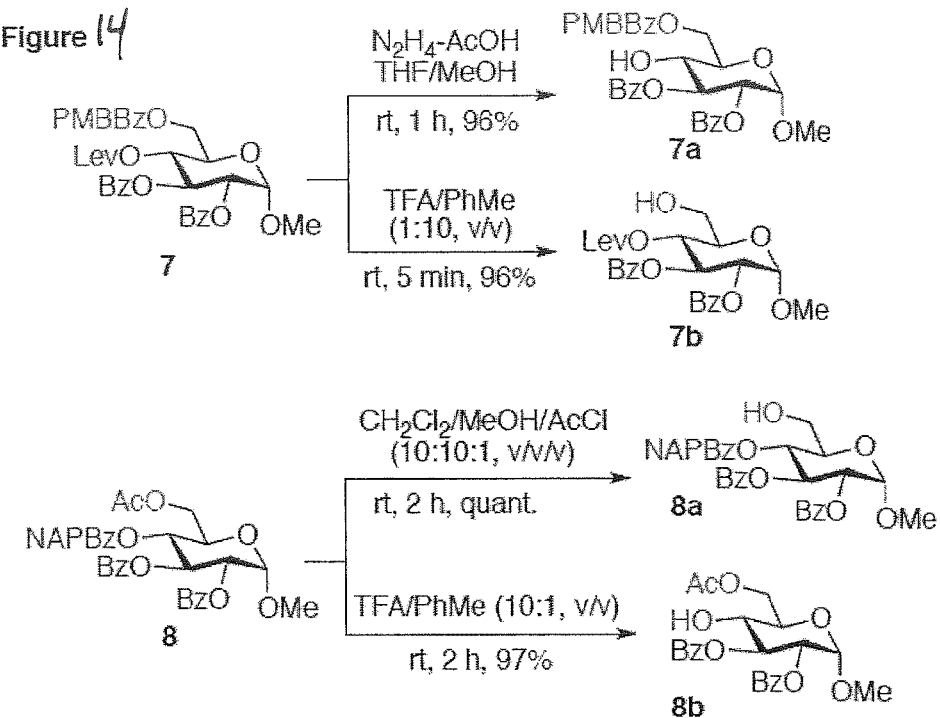
FIG. 14 shows that preferred acid-labile ester protecting groups of the present disclosure are chemically compatible as substitutes for other known protecting groups.

FIGS. 3-5 illustrate first preferred catalytic glycosylation methods of the present disclosure representing the first catalytic glycosylation methods featuring an anomerically stable thioether leaving group. The preferred catalytic glycosylation methods are modular both in terms of the glycosylating agent, where the backbone of thioaryl ether can be readily modified to change its reactivity and also the activator. The preferred catalytic glycosylation methods only require a single component cationic gold(I) complex as the activator, which is drastically different from conventional chemistry involving thioglycoside activation. The by-product generated in the preferred catalytic glycosylation methods of the present disclosure (benzothiophene) does not participate the glycosylation, which is different from known glycosyltrichloroimidate chemistry where the by-product trichloroacetamide can serve as competitive nucleophile to complicate the glycosylation reaction.

As shown in FIG. 6, the preferred catalytic glycosylation methods of the present disclosure permit the application of highly acid-sensitive protecting groups, described herein, as permanent protecting group. These types of -transformations cannot be routinely carried out with glycosyl imidates or conventional thiolgycoside.

FIGS. 7-8 illustrate additional preferred catalytic glycosylation methods of the present disclosure which permit the reactivity-based one-pot glycosylation that employs a single-component catalyst that dramatically accelerates the oligosaccharide assembly process. FIG. 7 shows reactivity based catalytic glycosylation while FIG. 8 illustrates reactivity based catalytic glycosylation to access blood antigen oligosaccharide.

The preferred catalytic glycosylation methods of the present disclosure which permit the application of 100%-PEG-based polymer as insoluble support for solid-phase oligosaccharide synthesis. This cannot be achieved with traditional oxophilic Lewis acid activator, as they will bind the PEG backbone and diminish their activities as activators. 100%-PEG-based polymer is marketed by Novabiochem and has been widely applied in peptide synthesis. The preferred designer thioglycosides of the present disclosure retain the basic properties of parental thioglycoside, including the ease of preparation and toleration of backbone protecting group manipulation, an essential feature for preparative purpose.

Novel Protecting Groups for Synthesis of Oligosaccharides and Natural Products

Figure 15:
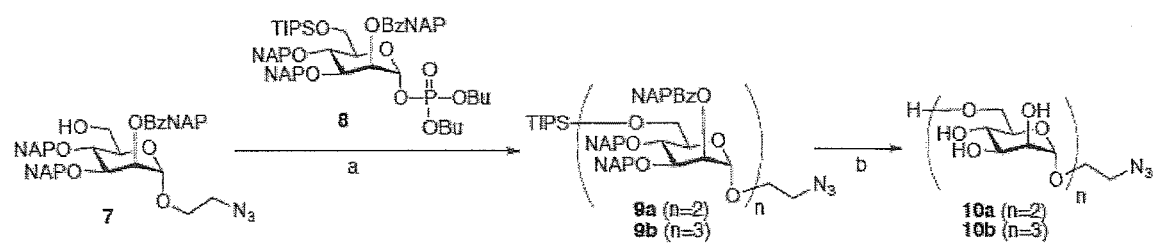
FIG. 15 illustrates shows that preferred acid-labile ester protecting groups of the present disclosure may be employed as a global protecting group protecting all hydroxyl groups on an oligosaccharide backbone according to preferred embodiments of the present disclosure.

The present disclosure preferably employs a series of ester-type of protecting groups that are used to mask hydroxyl functionalities. While traditional ester protecting groups require base treatment for removal, by tethering acetyl ester and benzoyl ester with an alcohol group that is protected with an acid-labile protecting group, the ester group can be readily deprotected by acid treatment. The preparation of this ester-protecting group is straightforward and it can be done on a multi-gram scale in a routine academic lab. By tuning the ester backbone as well as the tethered alcohol protecting group, a set of new acid-responsive ester protecting groups is preferably obtained. This not only can be used as temporary protecting group from complex carbohydrate and natural product synthesis, but can also be used as permanent protecting group for complex carbohydrate synthesis, as outlined in FIG. 15 showing the synthesis of an oligomannoside according to a preferred embodiment of the present disclosure.

FIG. 9 shows preferred processes for attaching the designed thioethers to carbohydrates and transforming to the designed glycosylating agents with respect to preferred catalytic glycosylation methods of the present disclosure. FIG. 10 illustrates the compatibility of preferred glycosylation agents to known protecting group manipulations for use in preferred catalytic glycosylation methods of the present disclosure.

The following examples/schemes, as depicted in FIGS. 11-15, illustrate preferred aspects of oligosaccharide synthesis using novel protecting groups of the present disclosure. The preferred embodiments of the present disclosure will streamline the synthesis of biologically important oligosaccharide by automation. To the best of the inventor's knowledge, no acid sensitive ester-type protecting group has ever been described in the context of complex molecule synthesis. The present disclosure allows for the dramatic enhancement of production efficiency of biologically active compounds in both industrial and academic labs which are oriented towards biological research.

It should be emphasized the technical difficulties associated with the preparation of oligosaccharides largely exceeds those of DNA, RNA and peptides. RNA, a homologue of DNA, but with an extra hydroxyl group at C-2 position of ribose, was once considered difficult to synthesize by automation, because of the lack of proper protecting group to mask that functionality.

It should be understood that while this disclosure has been described herein in terms of specific, preferred embodiments set forth in detail, such embodiments are presented by way of illustration of the general principles of the disclosure, and the disclosure is not necessarily limited thereto. Certain modifications and variations in any given material, process step or chemical formula will be readily apparent to those skilled in the art without departing from the true spirit and scope of the present disclosure, and all such modifications and variations should be considered within the scope of the claims that follow.

What is claimed is:

1. A catalytic glycosylation method comprising:
   installing thioether to an anomeric carbon of a carbohydrate; and
   catalytically activating the thioether with an activator comprising a non-oxophilic Lewis acid comprising a cationic gold(I) complex.

2. The catalytic glycosylation method of claim 1 further comprising:
   applying a 100%-PEG-based polymer as insoluble support for solid-phase oligosaccharide synthesis to streamline an oligosaccharide assembly.

3. The catalytic glycosylation method of claim 2 wherein the activator is carbophilic.

* * * * *